United States Patent [19]

Horodysky

[11] 4,212,753
[45] Jul. 15, 1980

[54] REACTION PRODUCTS OF SULFURIZED OLEFIN ADDUCTS OF PHOSPHORODITHIOIC ACIDS AND ORGANIC COMPOSITIONS CONTAINING SAME

[75] Inventor: Andrew G. Horodysky, Cherry Hill, N.J.

[73] Assignee: Mobil Oil Corporation, New York, N.Y.

[21] Appl. No.: 16,716

[22] Filed: Mar. 1, 1979

[51] Int. Cl.$^2$ .............................................. C10M 1/48
[52] U.S. Cl. .................................. 252/46.6; 252/46.7; 252/389 A; 252/400 A; 260/125; 260/139
[58] Field of Search ............ 252/32.7 HC, 46.6, 46.7, 252/389 A, 400 A; 260/125, 139

[56] References Cited

U.S. PATENT DOCUMENTS

| | | | |
|---|---|---|---|
| 2,799,653 | 7/1957 | Scanley | 252/32.7 HC |
| 2,897,228 | 7/1959 | Scott et al. | 252/46.6 X |
| 2,971,019 | 2/1961 | Ladd et al. | 252/46.6 X |
| 3,328,298 | 6/1967 | Asseff | 252/46.6 X |
| 3,574,795 | 4/1971 | Oswald et al. | 252/46.7 X |
| 3,644,206 | 2/1972 | Braid | 252/46.7 |
| 4,152,275 | 5/1979 | Horodysky et al. | 252/46.6 |

*Primary Examiner*—Andrew Metz
*Attorney, Agent, or Firm*—C. A. Huggett; R. W. Barclay; C. E. Setliff

[57] ABSTRACT

A novel product formed by reacting a reactive olefin, an epoxide or another reactive compound with the product of reaction between a dialkyl or diaryl phosphorodithioic acid and a sulfurized olefin possesses, among other things, good antiwear and antioxidant activity. Organic compositions containing a minor amount thereof possess good lubricating characteristics.

26 Claims, No Drawings

REACTION PRODUCTS OF SULFURIZED OLEFIN ADDUCTS OF PHOSPHORODITHIOIC ACIDS AND ORGANIC COMPOSITIONS CONTAINING SAME

BACKGROUND OF THE INVENTION

1. Field of the Invention

This invention is directed to novel compounds comprising reaction products made by reacting reaction products of alkyl or aryl phosphorodithioic acids and a sulfurized olefin with a reactive olefin, epoxide or other reactive compound.

2. Summary of the Prior Art

Sulfurized olefins are known to be effective extreme pressure agents or load carrying additives for lubricating oils. See U.S. Pat. Nos. 3,703,504; 3,697,499 and 3,471,404.

Phosphorodithioic acids have been reacted with olefins, as disclosed, for example, in U.S. Pat. Nos. 3,646,172 and 3,350,348, and A. A. Oswald, Journal Organic Chemistry, 27,2439 (1962). However, none of these processes are similar to the instant process nor are the compounds so produced similar to the novel adducts of this invention.

It has now been discovered that when the reaction product of certain olefinic compounds or epoxides are reacted with the reaction product of a dialkyl or diaryl phosphorodithioic acid and a sulfurized olefin, low phosphorus (0.1-10%), high sulfur (ca. 20% or more), low ash content products result. These products have improved oil solubility, odor, and copper strip corrosivity characteristics as compared to the sulfurized olefin and impart several desirable characteristics to organic substrates, e.g., lubricating oils, when incorporated therein.

SUMMARY OF THE INVENTION

This invention is directed to organothiophosphorus compounds comprising the product formed by reacting a diene, acrylonitrile, an unsaturated aldehyde or a compound having one of the formulae

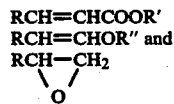

wherein R, R' and R" are hydrogen or are hydrocarbyl groups or substituted hydrocarbyl groups containing 1 to 30 carbon atoms, R and R' preferably being alkyl of 2 to 10 carbon atoms, R" preferably being alkyl, aryl, alkylaryl, or haloalkyl containing 2 to 10 carbon atoms and from 1 to 3 halo groups (e.g., Cl, Br, F) with the product of reaction between (1) a phosphorodithioic acid of the formula

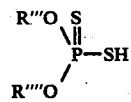

wherein R''' and R'''' are hydrocarbyl groups, either the same or different, having from 1 to 30 carbon atoms, and (2) a sulfurized olefin.

R''' and R'''' may each be alkyl of 1 to 30 carbon atoms, or they may be aryl, alkaryl or aralkyl of from 6 to 30. Accordingly, R''' and R'''' may be selected from the group consisting of methyl, ethyl, n-propyl, isopropyl, n-butyl, isobutyl, pentyl, hexyl, ethylhexyl, oleyl, octadecyl, eicosyl, triacontyl, phenyl, ethylphenyl, phenethyl and the like and mixtures thereof.

It is also contemplated that esters of acrylic acid and substituted acrylic acids, as well as acrylonitriles, unsaturated aldehydes, such as acrolein and acrolein dimer and dienes can be effectively used to prepare the product of the invention.

This invention is also directed to organic compositions comprising a major amount of an organic medium normally subject to deterioration and a minor amount of an additive sufficient to impart antiwear, antioxidant, detergent, extreme pressure and antirust characteristics thereto comprising an organothiophosphorus compound in accordance with this invention and wherein said organic medium is a lubricant from among oils of lubricant viscosity, hydrocracked oils, mineral oils or fractions thereof, synthetic oils or mixtures of synthetic and mineral oils, automotive oils, gear oils and transmission fluids, hydraulic oils, waxes and greases prepared from said oils of lubricating viscosity.

DESCRIPTION OF SPECIFIC EMBODIMENTS

The sulfurized olefin contains reactive olefinic sites and may be derived from a process comprising sulfohalogenating a hydrocarbon olefin having a single double bond and having from 2 to about 8 carbon atoms per molecule with a sulfur halide selected from the group consisting of sulfur chlorides and sulfur bromides to form a sulfohalogenated intermediate, and thereafter sulfurizing and dehalogenating said intermediate by treatment with an aqueous alkali metal monosulfide solution such as described in U.S. Pat. No. 3,703,504, but this class of reactant is not limited thereto. The alkali metal monosulfide solution may comprise sodium, potassium, or lithium sulfide and may contain sodium hydroxide, sodium hydrosulfide, sodium cresylates, sodium sulfate, sodium chloride, oil and ferrous sulfide. The sulfurized olefins made by variations of the process or by other processes known to the art which contain reactive olefinic sites and have a sulfur content of about 20% by weight and above may be employed in the invention. Dimethallyl sulfides such as

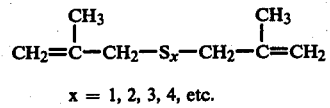

x = 1, 2, 3, 4, etc.

which can be formed by the reaction of methallyl chloride with an alkali metal monosulfide, alkali metal disulfide or alkali metal polysulfide may be employed in this invention.

The phosphorodithioic acids in accordance with this invention are generally prepared from the reaction of a suitable phosphorus sulfide, e.g., phosphorus pentasulfide, with a variety of phenolic or alcoholic materials, preferably a hydroxylic compound ROH where R may be aryl or alkyl of up to about 30 carbon atoms. A nonexhaustive list of suitable hydroxylic compounds include phenol, nonylphenol, dodecylphenol, methanol, ethanol, n-propanol, i-propanol, n-butanol, i-butanol, primary and secondary pentanols, hexanol, ethylhexanol, oleyl alcohol, eicosyl alcohol, triacontyl alcohol and mixtures thereof.

The preparation of the phosphorodithioic acids may be carried out in any convenient manner known to the art. These acids may also be obtained commercially or made, for example, by slowly reacting a mixture of phosphorus sulfide and the aforementioned hydroxylic component.

Sulfurized olefins useful herein are generally described in U.S. Pat. No. 3,703,504, the entirety of which is incorporated herein by reference. This class of reactant, however, is not limited thereto.

Generally speaking, the sulfurized olefins may be obtained via a process which comprises sulfohalogenating an olefin with a sulfur halide in the presence of a catalytic quantity (i.e., 0.2-10 wt. % based on the halide) of a lower aliphatic alcohol (such as methanol, ethanol, propanol, i-propanol, butanol, i-butanol, i.e., having up to about 10 carbon atoms) to form a sulfohalogenated organic intermediate, and thereafter sulfurizing and dehalogenating said intermediate in the presence of a substantial quantity of lower aliphatic alcohol, e.g., from 10 to about 50% by weight of the adduct, by treatment with an aqueous alkali metal sulfide solution, or an aqueous alkali metal monosulfide solution (which can be derived, for example, from a spent aqueous alkali metal hydroxide effluent from hydrocarbon purification) having a substantial combined sulfur content, thus producing an organic sulfide of high combined sulfur content.

A wide variety of olefinic substances may be charged to the initial sulfochlorination reaction, including olefins having a single double bond as terminal or internal double bonds. The olefinic substances usually contain from about 2 to 8 or more carbon atoms per molecule in either straight, branched chain or cyclic compounds. These may be exemplified by ethylene, propylene, butene-1, cis- and trans- butene-2, isobutylene, diisobutylene, triisobutylene, the pentenes, cyclopentene, the hexenes, cyclohexene, the octenes and decene-1. Isobutylene is generally the preferred olefinic reactant. In general $C_{3-6}$ olefins or mixtures thereof, are desirable for preparing sulfurized products for use herein as lube oil additives. The combined sulfur content of the product decreases with increasing carbon content while its miscibility with oil is lower for propylene and ethylene derivatives.

The other reactant in the first stage is preferably sulfur monochloride ($S_2Cl_2$), but other similar compounds, such as sulfur dichloride and $S_3Cl_2$ and the corresponding sulfur bromides, may be employed in an amount which will provide a quantity of sulfur corresponding to desirable reactant ratios for sulfur monochloride. The molar ratio of olefin to sulfur monohalide may range from about 1:1 up to 1.7:1 or more. In the case of isobutylene and sulfur monochloride, the optimum ratio appears to be between about 1.55:1 and 1.60:1.

The initial reaction can be catalyzed with a lower aliphatic alcohol containing from 1 to 4 carbon atoms, as exemplified by methanol, ethanol, propanol and isopropanol. Of these, methanol and ethanol are usually preferred. The spent aqueous alkali metal hydroxide effluent as mentioned hereinabove is derived primarily from spent organic caustic liquors issuing from integrated refinery processes.

The sulfurized olefins produced by the above-described process have a very high sulfur content of from about 20% by weight to about 55% by weight (typically about 46-48% combined sulfur) and are substantially devoid of free sulfur. Other sulfurized olefins made by variations of this process or by other processes known to the art which contain reactive olefinic sites and have a sulfur content of about 20% and above may also be employed in this invention. The novel compounds of this invention may thus be prepared from the intermediate formed by adding phosphorodithioic acids in low concentrations to such sulfurized olefins. These compounds have a low phosphorus content, i.e., from about 0.1 to about 10 weight percent, and a high sulfur content of about 20 to about 50% by weight. The low phosphorus content inter alia may account for improved low solubility, improved odor and improved copper strip corrosivity.

The reaction to make the phosphorodithioic acid-sulfurized olefin intermediate is usually carried out at temperatures of from about 75° to 150° C., preferably from 80°-110° C., under atmospheric pressure (although higher pressures may be used if desired) for periods of up to about 16-20 hours, e.g., preferably from about 1 to about 10 hours or more. The reaction mixture is heated with agitation to the desired temperature. The reaction may be accelerated by sparging catalytic amounts of hydrogen sulfide to the reaction vessel to increase the product yield. The reaction may also be carried out in the absence of any added solvent or it may be carried out in a non-reactive solvent such as pentane, hexane, heptane, cyclohexane, benzene, toluene and the like or a refined petroleum oil may be employed therefor.

As indicated in the Summary, the phosphorodithioic acid-sulfurized olefin adduct may be reacted with a vinyl ester, a vinyl ether or an epoxide. The reactants also include acrylonitrile and unsaturated aldehydes of the formula

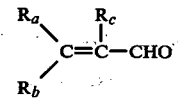

wherein $R_a$, $R_b$ and $R_c$ can be the same or different and are aryl having 6 to 10 carbon atoms (e.g., phenyl and naphthyl) or alkyl having 1 to 10 carbon atoms, such as acrolein. $R_c$ and one of $R_a$ and $R_b$ may also be hydrogen. The reactants further include the dienes, which may have up to 15 carbon atoms.

Included among the esters are vinyl acetate, vinyl propionate, vinyl benzoate, vinyl butyrate and the like. Some of the ethers contemplated are 2-ethylhexyl vinyl ether, butyl vinyl ether and vinyl anisole. Epoxides include ethylene, propylene and butylene oxides.

The reaction with the ester, ether, or epoxide or other unsaturated moiety is carried out at a temperature of from about 50° C. to about 150° C., preferably from about 70° C. to about 110° C. The time of reaction will range from about 1 to about 30 hours, preferably from about 1 to about 8 hours.

Desirable solvents which can be used include hydrocarbon solvents such as hexane, benzene, toluene, etc. or alcoholic solvents such as methanol, ethanol, propanol, isopropanol, butanol, etc. The preferred solvent is isopropanol.

The novel non-metallic compounds comprising the reaction product as described hereinbefore between vinyl ester, vinyl ether, acrylonitrile, unsaturated aldehyde, dienes, terpenes, or epoxide and an adduct of dialkyl or diaryl phosphorodithioic acid with sulfurized olefins (such as those sulfurized olefins disclosed in U.S. Pat. No. 3,703,504) may be used effectively to impart to organic media, particularly to lubricating oils and greases, the properties mentioned hereinabove. An effective amount of the additive compound for all of the properties mentioned above will range from about 0.01% to about 10% by weight. Preferably the organic medium or substrate, e.g., oil of lubricating viscosity, contains from about 0.1 to 5% and more preferably from about 0.5 to about 2% by weight of the total weight of the lubricant composition. As hereinbefore indicated, the organic sulfur- and phosphorus-containing complexes may be incorporated into any lubricating media, which can include oils of lubricating viscosity and also greases in which any of the aforementioned oils are employed as vehicles. In general, synthetic oils can also be effectively protected against the above-noted deterioration or degradation. They may also be employed in combination with mineral oils, and ester base stock, or as grease vehicles. Typical synthetic vehicles include polyisobutylene, polybutenes, polydecene, hydrogenated polydecenes, polypropylene glycol, polyethylene glycol, trimethylolpropane esters, neopentyl alcohol, and pentaerythritol esters, di(2-ethylhexyl) sebacate, di(2-ethylhexyl) adipate, dibutyl phthalate, fluorocarbons, esters of phosphorus-containing acids, liquid ureas, ferrocene derivatives, hydrogenated mineral oils, chain-type polyphenols, siloxanes and silicones (polysiloxanes), alkyl-substituted diphenyl ethers, typified by a butyl-substituted bis-(p-phenoxyphenyl)ether and phenoxyphenyl ether.

The following Examples 1 through 11 illustrate the preparation of the product of the invention. Examples 1-4 show the preparation of the intermediate.

EXAMPLE 1

Sulfurized olefin was prepared in accordance with Example 1 of U.S. Pat. No. 3,703,504 using isobutylene. The yield of sulfurized organic product amounted to 98% of theory, had a sulfur content of 47% by weight and a chlorine content of only 0.11%, as well as a clear, light orange-brown color, and a high flash point of 250° F.

EXAMPLE 2

Sulfurized olefin was prepared in general accordance with Example 6 of U.S. Pat. No. 3,703,504. A mixture of butylenes was sulfurized using the same reaction conditions described and an equivalent molar ratio of flake sodium monosulfide (Na$_2$S). The olefin mixture employed in this instance had the following composition by volume:

| Component | Volume Percent |
| --- | --- |
| Isobutylene | 90.5 |
| Trans-2-butane | 5.9 |
| Cis-2-butene | 2.6 |
| Butadiene | 1.0 |
| | 100.0 |

The product had the following characteristics:

| Sulfur content, wt. % | 45.87 |
| --- | --- |
| Chlorine content, wt. % | 0.27 |
| Viscosity | 12.1 cs/210° F. |

EXAMPLE 3

O-2-propyl O-2-ethylhexylphosphorodithioic acid was made by the reaction of an equal molar mixture of 2-propanol and 2-ethylhexanol with an excess of phosphorus pentasulfide (added over one hour at 70°–80° C.). The reaction mixture was further agitated at 75°–80° C. for 2 more hours. After the evolution of H$_2$S stopped, the reaction mixture was cooled and the unreacted phosphorus pentasulfide was removed by filtration. Approximately 3,200 grams of the sulfurized olefin prepared in accordance with Example 1 was then reacted with 935 grams of the mixed O-2-propyl O-2-ethylhexyldiphosphorodithioic acid to form a phosphorus- and sulfur-containing adduct by reaction at 85°–100° C. for about 5 hours with agitation and a slow H$_2$S sparge. The crude reaction product was sparged for one more hour with N$_2$ to remove any excess H$_2$S.

| Product Analysis: | |
| --- | --- |
| Phosphorus, wt. % | 2.0 |
| Sulfur, wt. % | 35.1 |
| Carbon, wt. % | 49.9 |
| Hydrogen, wt. % | 8.2 |

EXAMPLE 4

O,O-di-4-methyl-2-pentylphosphorodithioic acid was made by the reaction of 4-methyl-2-pentanol with an excess of phosphorus pentasulfide at 75°–80° C. After the evolution of H$_2$S diminished, the reaction mixture was cooled, and unreacted phosphorus pentasulfide was removed by filtration. Approximately, 3,600 grams of the sulfurized olefin prepared in accordance with Example 2 was then reacted with 1,060 grams of O,O-di-4-methyl-2-pentylphosphorodithioic acid to prepare a phosphorus- and sulfur-containing product by reaction at 90°–100° C. for about 6 hours with agitation and a slow H$_2$S sparge. The crude reaction product was then sparged for one more hour with N$_2$ to remove any excess H$_2$S.

Product Analysis 33.4% Sulfur
1.8% Phosphorus
0.1% Chlorine
43.1% Carbon
7.1% Hydrogen

EXAMPLE 5

Approximately 105 grams of O-2-propyl O-2-ethylhexylphosphorodithioic acid-sulfurized olefin intermediate, made following the procedure of Example 3, was charged to a reactor and heated up to 70°–75° C. with agitation. Over a period of 1 hour, 15 grams of vinyl acetate was slowly added dropwise. Agitation was continued for 2.5 additional hours at 75°–85° C. The unreacted excess of vinyl acetate was then removed by vacuum distillation at about 85° C. and the orange liquid was clarified by filtration.

Product Analysis 36.7% Sulfur
2.0% Phosphorus
0.1% Chlorine
51.6% Carbon 7.8% Hydrogen

EXAMPLE 6

Approximately 125 grams of mixed O-2-propyl O-2-ethylhexylphosphorodithioic acid-sulfurized olefin intermediate prepared using the procedure described in Example 3 was charged to a reactor and heated to 80° C. with agitation. The addition of 13 grams of n-butyl vinyl ether was performed dropwise over a period of 1 hour. The reaction mixture was then agitated at 90°–100° C. for 4.5 additional hours, during which time the reaction mixture deepened in color. A vacuum stripping was performed at 95°–100° C. to remove unused reactants. The product was then filtered over a bed of diatomaceous earth. A viscous liquid was recovered.

Product Analysis 29.6% Sulfur
1.7% Phosphorus
0.1% Chlorine
50.6% Carbon
8.2% Hydrogen

EXAMPLE 7

O-2-propyl O-2-ethylhexylphosphorodithioic acid-sulfurized olefin intermediate was prepared as described in Example 3. Approximately 125 grams of this intermediate was charged to a reactor and heated to 75° C. with agitation. Over a period of about 0.75 hour approximately 10 grams of 2-chloroethyl vinyl ether was added. After the addition was completed, the mixture was reacted at 85°–90° C. for an additional 4.5 hours. A vacuum topping was performed at 95°–100° C. to remove unreacted starting materials and the liquid product was filtered over a bed of diatomaceous earth.

Product Analysis 31.4% Sulfur
1.7% Phosphorus
1.1% Chlorine
48.9% Carbon
8.1% Hydrogen

EXAMPLE 8

O-2-propyl O-2-ethylhexylphosphorodithioic acid-sulfurized olefin intermediate was prepared as described in Example 3. A reactor was charged with 125 grams of this intermediate and the contents were heated to 70° C. with agitation. Over a period of 1 hour, 12 grams of propylene oxide was slowly added dropwise. The reactants were then agitated at 70°–80° C. for an additional 4.5 hours. The crude mixture was vacuum stripped at 90°–100° C. to remove unreacted volatile material and then filtered. The product was an orange liquid.

Product Analysis 32.4% Sulfur
1.9% Phosphorus
0.1% Chlorine
48.0% Carbon
7.8% Hydrogen

EXAMPLE 9

Approximately 125 grams of O,O-di-4-methyl-2-pentylphosphorodithioic acid intermediate prepared following the procedure described in Example 4 was charged to a reactor and heated to about 60° C. with agitation. Over a period of 1 hour, 10 grams of propylene oxide was slowly added dropwise. The reactants were heated for 4 additional hours at 85°–95° C. with agitation. A vacuum distillation was performed at 90°–100° C. to remove unreacted volatile materials and the orange liquid product was filtered over a bed of diatomaceous earth.

Product Analysis 34.3% Sulfur
1.8% Phosphorus
0.1% Chlorine
48.9% Carbon
7.9% Hydrogen

EXAMPLE 10

O-2-propyl O-2-ethylhexylphosphorodithioic acid-sulfur olefin intermediate was prepared as described in Example 3. A reactor filled with a condenser was charged with 125 grams of this intermediate and the contents were heated to 70°–75° C. with agitation. Approximately 13 grams of butylene oxide (1,2-butane oxide) was added dropwise over a period of ½ hour. The reaction mixture was heated to 85° C. and held at 85°–95° C. for 5.5 additional hours with agitation. Unreacted volatile material was removed by vacuum topping at 95°–105° C. and the orange-brown liquid product was filtered over diatomaceous earth.

Product Analysis 33.2% Sulfur
1.9% Phosphorus
0.1% Chlorine
48.9% Carbon
8.1% Hydrogen

EXAMPLE 11

Approximately 110 grams of the O-2-propyl O-2-ethylhexylphosphorodithioic acid prepared as described in Example 3 was charged to a reactor fitted with a condenser and heated to about 70° C. with agitation. Over a period of 1.5 hours, 20 grams of methyl acrylate was slowly added dropwise. The reaction mixture was then held at 95°–100° C. for 3.5 additional hours with agitation. Unreacted volatile materials were removed by vacuum distillation at 100°–105° C. and the orange liquid was filtered over diatomaceous earth.

Product Analysis 36.1% Sulfur
2.0% Phosphorus
0.1% Chlorine
53.8% Carbon
8.7% Hydrogen Selected compounds from the above Examples were tested in oil compositions in accordance with the following tests:

Copper Corrosion

Representative samples of the above prepared adducts were tested at 1% (by weight) for copper corrosivity using ASTM No. D130-9 at 210° F. for 6 hours. The base oil was 200-second solvent paraffinic neutral mineral oil. The results are summarized in Table 1.

Table 1

| Additive, Example | Rating |
|---|---|
| 3 | 2D |
| 4 | 2C |

Table 1-continued

| Additive, Example | Rating |
| --- | --- |
| 5 | 2C |
| 6 | 2A |
| 7 | 3A |
| 8 | 2A |
| 9 | 2A |
| 10 | 2A |
| 11 | 2C |

Catalytic Oxidation

A sample of the base lubricant was placed in an oven at a desired temperature. Present in the same were the following metals either known to catalyze organic oxidation or commonly used materials of construction.
a. 15.6 sq. in. of sand-blasted iron wire,
b. 0.78 sq. in. of polished copper wire,
c. 0.87 sq. in. of polished aluminum wire, and
d. 0.167 sq. in. of polished lead surface.

Dry air was passed through the sample at a rate of about 5 liters per hour. The temperature was 325° C. and the test was carried out for 40 hours.

The results of this test are summarized in Table 2. The oil used in all tests was a solvent paraffinic neutral 200 second mineral oil. The additive concentration in each case was 1% by weight.

TABLE 2

| Additive, Example | Visc. Incr. %, 100° C. | Neut. No. | Lead Loss, Mg. |
| --- | --- | --- | --- |
| ,—(a) | .29 | 2.21 | 0.4 |
| 5 | 20 | 1.27 | 0 |
| 6 | 26 | 1.49 | 0 |
| 7 | 27 | 1.66 | 0 |
| 8 | 21 | — | 0 |
| 9 | 26 | 1.48 | 0 |
| 10 | 22 | 1.45 | 0 |
| 11 | — | 1.57 | 0 |

(a) Blank (base oil)

Shell 4-Ball

In this test, three stationary balls are placed in a lubricant cup and a lubricant containing the additive to be tested is added thereto. A fourth ball is placed on a chuck mounted on a device which can be used to spin the ball at known speeds and loads.

One percent by weight of the product was placed in a blend of a 150″ (210° F.) solvent paraffinic bright mineral oil and a 200″ (100° F.) solvent paraffinic neutral mineral oil. These oils were blended in a ratio of 80/20, respectively. The balls used were ½ inch 52100 steel. Table 3 summarizes the results of tests carried out at varying temperatures, at a 60 kg. load and for 30 minutes per test.

TABLE 3

| Additive Example | Temp., °F. | Speed, RPM 600 | 1200 | 1800 |
| --- | --- | --- | --- | --- |
| (a) | Room | 0.,60 | 0.75 | 0.90 |
|  | 200 | 0.70 | 2.00 | 2.45 |
|  | 350 | 1.65 | 2.00 | 2.48 |
| 5 | Room | 0.50 | 0.60 | 0.80 |
|  | 200 | 0.55 | 0.80 | 1.00 |
|  | 350 | 0.75 | 1.63 | 1.88 |

(a) Blank (base oil)

Thermal Oxidation

This test uses a differential scanning calorimeter to measure oxidation. Briefly, a sample containing additive is placed in a sample cup, and the test is begun at atmospheric pressure and ambient temperature. The oxygen pressure is gradually increased to 38 psi and the temperature is programmed to rise to a maximum of 170° C. Another sample containing no additive is placed alongside the test sample. From the differential scanning calorimeter, one obtains an S-shaped curve from which can be obtained the start of oxidation ($t_o$), time to midpoint ($t_{\frac{1}{2}}$) and completion of oxidation ($t_f$). The oil used was a synthetic hydrocarbon fluid (polydecene trimer). The results are shown in Table 4.

TABLE 4

| Additive, Example | Conc., % wt. | $t_o$, min. | $t_{\frac{1}{2}}$, min. | $t_f$, min. |
| --- | --- | --- | --- | --- |
| 1 | 0.25 | 20 | 34 | 41 |
| 5 | 0.25 | 50 | 72 | 80 |
|  | 0.30 | 82 | 97 | 105 |
| 11 | 0.25 | 27 | 48 | 55 |

The data shown in the tables clearly establish that the novel compounds of this invention provide good antioxidant and antiwear properties to lubricants while maintaining or improving good copper strip corrosivity.

While the present invention has been described in detail in conjunction with the treatment of a limited number of compounds under similar conditions for the purposes of valid comparisons and of fully illustrating the invention, it will be readily apparent to those of ordinary skill in the art that numerous modifications and variations are within the purview of this invention.

I claim:

1. A product made by reacting diene, acrylonitrile, an unsaturated aldehyde or a compound selected from the formulae

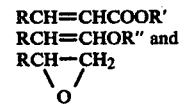

wherein R, R' and R" are hydrogen or hydrocarbyl groups or substituted hydrocarbyl groups containing 1 to 30 carbon atoms with the reaction product of
(1) a phosphorodithioic acid of the formulae

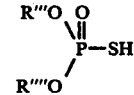

wherein R'" and R"" are hydrocarbyl groups containing 1 to 30 carbon atoms and
(2) a sulfurized olefin.

2. The product of claim 1 wherein R and R' have from 2 to 10 carbon atoms and R" has from 2 to 10 carbon atoms and from 1 to 3 halogen atoms.

3. The product of claim 1 wherein R'" and R"" are alkyls of from 1 to 30 carbon atoms or aryl, alkaryl or aralkyl of from 6 to 30 carbon atoms.

4. The product of claim 1 wherein the sulfurized olefin is made by sulfohalogenation of an olefin having from 2 to 8 carbon atoms.

5. The product of claim 4 wherein said sulfurized olefin has a sulfur content of at least 20% by weight.

6. The product of claim 1 wherein the phosphorodithioic acid is O-2-propyl O-2-ethylhexyl phosphorodithioic acid.

7. The product of claim 1 wherein the phosphorodithioic acid is O,O-di(4-methyl-2-pentyl) phosphorodithioic acid.

8. The product of claim 1 wherein the said compound is vinyl acetate.

9. The product of claim 1 wherein the said compound is vinyl ether.

10. The product of claim 1 wherein the said compound is 2-chloroethyl vinyl ether.

11. The product of claim 1 wherein the said compound is propylene oxide.

12. The product of claim 1 wherein the said compound is butylene oxide.

13. The product of claim 1 wherein the said compound is methyl acrylate.

14. A lubricant composition comprising a major proportion of an oil of lubricating viscosity or greases prepared therefrom and an antioxidant, an antiwear or a copper corrosion inhibiting amount of a product made by reacting diene, acrylonitrile, an unsaturated aldehyde or a compound selected from the formulae

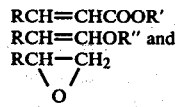

wherein R, R' and R" are hydrogen or hydrocarbyl groups or substituted hydrocarbyl groups containing 1 to 30 carbon atoms with the reaction product of (1) a phosphorodithioic acid of the formula

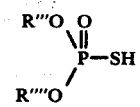

wherein R''' and R'''' are hydrocarbyl groups containing 1 to 30 carbon atoms and (2) a sulfurized olefin.

15. The composition of claim 14 wherein R and R' have from 2 to 10 carbon atoms and R" has from 2 to 10 carbon atoms and from 1 to 3 halogen atoms.

16. The composition of claim 14 wherein R''' and R'''' are alkyls of from 1 to 30 carbon atoms or aryl, alkaryl or aralkyl of from 6 to 30 carbon atoms.

17. The composition of claim 14 wherein the sulfurized olefin is made by sulfohalogenation of an olefin having from 2 to 8 carbon atoms.

18. The composition of claim 17 wherein said sulfurized olefin has a sulfur content of at least 20% by weight.

19. The composition of claim 14 wherein the phosphorodithioic acid is O-2-propyl O-2-ethylhexyl phosphorodithioic acid.

20. The composition of claim 14 wherein the phosphorodithioic acid is O,O-di(4-methyl-2-pentyl) phosphorodithioic acid.

21. The composition of claim 14 wherein the said compound is vinyl acetate.

22. The composition of claim 14 wherein the said compound is vinyl ether.

23. The composition of claim 14 wherein the said compound is 2-chloroethyl vinyl ether.

24. The composition of claim 14 wherein the said compound is propylene oxide.

25. The composition of claim 14 wherein the said compound is butylene oxide.

26. The composition of claim 14 wherein the said compound is methyl acrylate.